(12) United States Patent
Wang et al.

(10) Patent No.: US 9,669,004 B2
(45) Date of Patent: *Jun. 6, 2017

(54) DAIDZEIN ANALOGS AS TREATMENT FOR CANCER

(71) Applicants: THE ADMINISTRATORS OF THE TULANE EDUCATIONAL FUND, New Orleans, LA (US); UNITED STATES DEPARTMENT OF AGRICULTURE, New Orleans, LA (US); XAVIER UNIVERSITY OF LOUISIANA, New Orleans, LA (US)

(72) Inventors: Guangdi Wang, New Orleans, LA (US); Matthew E. Burow, New Orleans, LA (US); Stephen M. Boue, New Orleans, LA (US); Thomas E. Wiese, New Orleans, LA (US); Quan Jiang, New Orleans, LA (US)

(73) Assignees: The Administrators of the Tulane Educational Fund, New Orleans, LA (US); United States Department of Agriculture, New Orleans, LA (US); Xavier University of Louisiana, New Orleans, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/597,252

(22) Filed: Jan. 15, 2015

(65) Prior Publication Data

US 2015/0148409 A1 May 28, 2015

Related U.S. Application Data

(62) Division of application No. 13/808,918, filed as application No. PCT/US2011/043417 on Jul. 8, 2011, now Pat. No. 8,962,679.

(60) Provisional application No. 61/399,226, filed on Jul. 8, 2010.

(51) Int. Cl.
| | |
|---|---|
| *C07D 311/38* | (2006.01) |
| *A61K 31/353* | (2006.01) |
| *A61K 31/352* | (2006.01) |
| *C07D 493/04* | (2006.01) |

(52) U.S. Cl.
CPC .......... *A61K 31/353* (2013.01); *A61K 31/352* (2013.01); *C07D 311/38* (2013.01); *C07D 493/04* (2013.01)

(58) Field of Classification Search
CPC .................................................. C07D 311/38
See application file for complete search history.

(56) References Cited

U.S. PATENT DOCUMENTS

| | | | |
|---|---|---|---|
| 5,639,785 | A | 6/1997 | Kung |
| 7,008,649 | B2 | 3/2006 | Bessette et al. |
| 7,291,650 | B2 | 11/2007 | Bessette et al. |
| 8,080,675 | B2 | 12/2011 | Heaton et al. |
| 8,163,795 | B2 | 4/2012 | Heaton et al. |
| 2010/0069478 | A1 | 3/2010 | Kohen et al. |

FOREIGN PATENT DOCUMENTS

WO  WO 2009049214 A2 *  4/2009  ........... A61K 31/166

OTHER PUBLICATIONS

Gil, E. "Targeting the PI3K/AKT/mTOR pathway in estrogen receptor-positive breast cancer." Cancer Treatment Reviews. (2014), vol. 40, pp. 862-871.*
"Administration of drugs 3: parenteral." Nursing Times. Sep. 10, 2011. Available from: < https://www.nursingtimes.net/administration-of-drugs-3-parenteral/5034777.article >.*
National Cancer Institute. "Stomach (Gastric) Cancer-Patient Version." © 2016. Available from: < https://www.cancer.gov/types/stomach >.*
Heaton et al., (2006): STN International HCAPLUS database, (Columbus, Ohio), Accession No. 2006:295503.
International Preliminary Report on Patentability, Containing the Written Opinion, for PCT/US2011/043417, Issued Jan. 8, 2013.
Cottiglia et al., "New cytotoxic prenylated isoflavanoids from Bituminaria morisiana", Planta Medica (2005), vol. 71, No. 3, pp. 254-260, ISSN: 0032-0943.
International Search Report for PCT/US2011/043417 mailed Apr. 24, 2012 (5 pages).
Notification of Transmittal of the Interntional Search Report and Written Opinion for PCT/US2011/043417 mailed Apr. 24, 2012 (6 pages).

* cited by examiner

*Primary Examiner* — Noble Jarrell
*Assistant Examiner* — John S Kenyon
(74) *Attorney, Agent, or Firm* — McBee Moore Woodward & Vanik IP, LLC

(57) ABSTRACT

Provided are compositions for treatment of cancers, including breast cancer, comprising at least one novel daidzein analog, as well as methods of using the same for preventing or treating cancer or tumor growth.

24 Claims, 8 Drawing Sheets

(Daidzein)

(2)

(3a)

(3b)

(3c)

(3d)

(3e)

(3f)

(3g)

(3h)

DAIDZEIN ANALOGS AS TREATMENT FOR CANCER

CROSS-REFERENCE TO RELATED APPLICATIONS

This Application is a divisional application of U.S. application Ser. No. 13/808,918, filed Mar. 29, 2013, which is a 371 National Stage of PCT/US2011/043417, filed Jul. 8, 2011, which claims the benefit of U.S. Provisional Patent Application No. 61/399,226, filed under 35 U.S.C. §111(b) on Jul. 8, 2010, all of which are hereby incorporated by reference in their entirety.

BACKGROUND

1. Field

The present disclosure relates to the synthesis of novel daidzein analogs as a method of treating and preventing breast cancer.

2. Description of Related Art

Breast cancer remains the predominant form of carcinoma affecting American women today and resistance to chemo- and endocrine therapy is a major cause of treatment failure in breast cancer. Worldwide, more than 1 million women are diagnosed with breast cancer every year, accounting for one-tenth of all new cancers and 23% of all female cancer cases. In 2009 alone there were an estimated 192,370 new cases of breast cancer and 40,610 deaths from the disease. Recent estimates of the lifetime risk of developing breast cancer for women born in the United States is now 1 in 8, an increase from 1 in 10 during the 1970s. Short of prevention, detection of breast cancer at an early, still curable stage would offer the best route to decrease its mortality rates. However, only 63% of breast cancers are still confined to the breast at the time of diagnosis. In addition, despite the survival benefit achieved by regional treatment and adjuvant systemic therapy, 30-50% of breast cancer patients will eventually develop metastatic relapse and die, while a small percentage of patients would have survived without these treatment modalities. Hence, better markers for early diagnosis, accurate prognosis and prediction of response to treatment are warranted to improve breast cancer care.

Treatment options traditionally include surgical intervention, chemotherapy, radiation therapy, and adjuvant systematic therapies. Breast-conserving surgery (lumpectomy) followed by local radiation therapy has replaced mastectomy as the preferred surgical approach for treating women with early stage breast cancer. Adjuvants may include but are not limited to chemotherapy, radiation therapy, and endocrine therapies such as administration of LHRH agonists; antiestrogens, such as tamoxifen; high-dose progestogens; adrenalectomy; and/or aromatase inhibitors.

Endocrine therapy has emerged as a promising new way to combat certain cancers. By blocking hormones that encourage cell growth and proliferation, endocrine therapy has been shown to be effective in preventing the growth of several carcinomas, including those developing in the breast and prostate. The administration of endocrine therapy for breast cancer is dependent on the presence of estrogen receptors on cancer cells. Growth of cancers cells that are estrogen receptor positive is affected by the level of estrogen. By contrast, growth of estrogen receptor negative cells is largely independent of estrogen levels. An endocrine therapy, comprised of selective estrogen receptor modulators (SERMs), is given to patients diagnosed with estrogen receptor positive breast cancer. Tamoxifen is the pharmaceutical composition used as a SERM for breast cancer treatment, and acts as an estrogen antagonist on breast tissue.

Tamoxifen has been shown to drastically reduce incidences of treatment failure in patients diagnosed with estrogen receptor positive breast cancer. Tamoxifen is also given to women who have a high genetic disposition for breast cancer as a preventative measure. While effective against forms of breast cancer, Tamoxifen acts as an agonist on uterine tissue and promotes endometrial cell proliferation, increasing the risk of uterine cancer in women. Furthermore, Tamoxifen has also been shown to increase the risk of blood clots. The National Cancer Institute has stated the need for better SERMs for use in the treatment of breast cancer.

There is a need to develop new SERMs to treat estrogen receptor positive breast cancer. Thus, in view of the antiestrogen effects and ability to inhibit cell proliferation, the efficacy of novel daidzein analogs as a novel therapy in vivo was determined.

While certain novel features of this disclosure shown and described below are pointed out in the annexed claims, the disclosure is not intended to be limited to the details specified, since a person of ordinary skill in the relevant art will understand that various omissions, modifications, substitutions and changes in the forms and details of the disclosure illustrated and in its operation may be made without departing in any way from the spirit of the present disclosure. No feature of the disclosure is critical or essential unless it is expressly stated as being "critical" or "essential."

BRIEF SUMMARY OF THE INVENTION

The present disclosure provides novel daidzein analogs that have been discovered to have inhibitory effects on cell-proliferation, estrogen-induced transcriptional activity, and estrogen receptor regulated progesterone receptor gene expression. These analogs would thus be useful in the prevention and treatment of estrogen receptor positive breast cancer. In accordance with this discovery, it is an object of the disclosure to provide at least one novel daidzein analog. The at least one novel daidzein analog may be at least one isolated novel daidzein analog.

An object of the disclosure is to provide a composition, for example a pharmaceutical composition, comprising at least one novel daidzein analog in an amount effective for preventing or minimizing the development or growth of a cancer, which may be a primary cancer or a secondary (metastatic) lesion thereof. The cancer may be breast cancer, gastric carcinoma, ovarian cancer, pancreatic cancer, stomach cancer, non-small-cell lung cancer, or any cancer involving aberrant activation of the PI3K/AKT/mTOR pathway. An object of this disclosure is a kit, comprising a composition comprising at least one novel daidzein analog for preventing or minimizing the development or growth of breast cancer. The composition may comprise at least one carrier, at least one binder, at least one diluent, at least one excipient, or mixtures thereof.

Also provided are methods of preventing or treating cancer or tumor growth in a mammal comprising administering to the mammal an effective amount of a composition comprising at least one novel daidzein analog, and determining the development or growth of cancer has been prevented, minimized, or reversed.

In certain aspects, the at least one novel daidzein analog has a purity of ≥75%, ≥80%, ≥85%, ≥90%, ≥95%, ≥96%, ≥97%≥98%, and preferably ≥99%.

Other objects and advantages of this disclosure will become readily apparent from the ensuing description.

BRIEF DESCRIPTION OF THE DRAWINGS

FIG. 6D, FIG. 6E and FIG. 6F depict the hydrogen bond interactions made by the compounds daidzein, 3a and 2, respectively, with the protein as a ribbon/tube model colored by secondary structure and the compounds as ball & stick models.

DETAILED DESCRIPTION OF THE INVENTION

Figure 1:
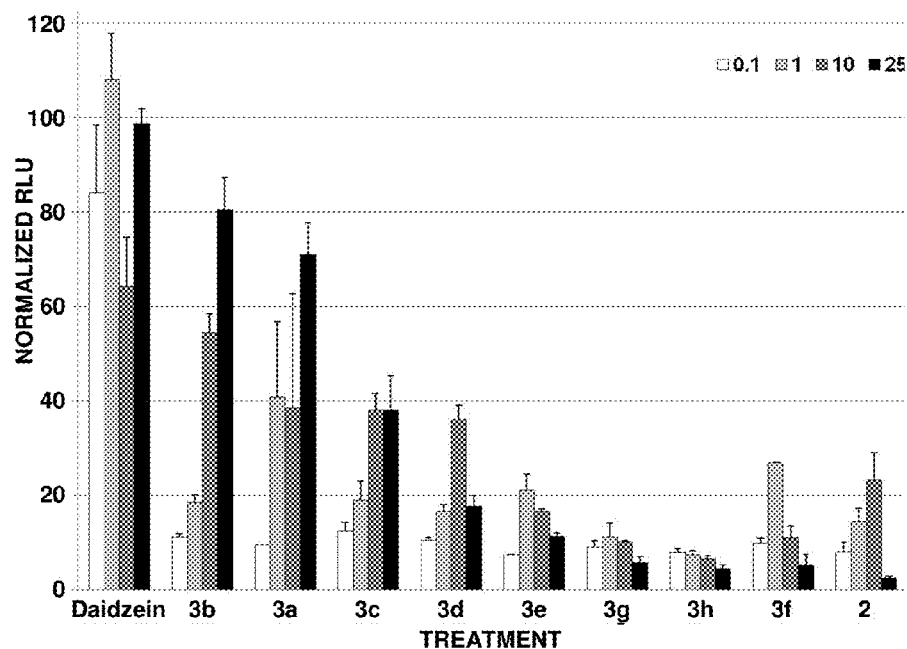
FIG. 1 shows the effects of daidzein and daidzein analogs on ERE transcriptional activity in MCF-7 cells. MCF-7 cells were transiently transfected with pGL2-ERE2x-TK-luciferase plasmid. After a 6 h transfection, cells were treated with compounds (DMSO, daidzein and daidzein analogs) and incubated overnight. Data are represented as relative light units (RLUs) normalized to $E_2$ (100±SEM). The values are the means and the SEM of triplicates from a single experiment and representative for at least three independent experiments. a: significant difference from daidzein, $p<0.05$; b: significant difference from daidzein, $p<0.01$; c: significant difference from daidzein, $p<0.001$.

Detailed descriptions of one or more preferred embodiments are provided herein. It is to be understood, however, that the present disclosure may be embodied in various forms. Therefore, specific details disclosed herein are not to be interpreted as limiting, but rather as a basis for the claims and as a representative basis for teaching one skilled in the art to employ the present disclosure in any appropriate manner.

This disclosure describes the synthesis of novel daidzein analogs and their antiestrogenic activity, as well as their marked effects on breast cancer cells. To fully understand the role of these analogs' anti-cancer properties, the relative affinity of daidzein analogs on estrogen receptor α, regulation of ER-mediated progesterone receptor gene expression by daidzein analogs, and the effect of daidzein analogs on estrogen receptor transcriptional activity and estrogen-stimulated clonogenic proliferation were studied.

As used herein, the term "breast cancer" refers to any cancer having its origin in breast cells, and includes metastatic and local forms of breast cancer. The term "minimize" or "reduce," or a derivative thereof, includes a complete or partial inhibition of a specified biological effect (which is apparent from the context in which the term minimize is used). An "effective amount" or "amount effective" with respect to the subject compositions and methods refers to an amount of the at least one novel daidzein analog in the subject compositions which, when administered as part of a desired dosage regimen (to a mammal, preferably a human) alleviates a symptom, ameliorates a condition, or slows the onset of disease conditions according to clinically acceptable standards for the disorder or condition to be treated, e.g., at a reasonable benefit/risk ratio applicable to any medical treatment. The term "mammal in need thereof" is a mammal diagnosed with a cancer, likely to develop a cancer, or is suspected of having a cancer.

Applicants modified the 7-hydroxyl functional group of daidzein while keeping the daidzein skeleton intact. Applicants began with an analog that is structurally identical with glyceollin I on the 7 and 8 ring substitutions but without the pterocarpan moiety. Using molecular modeling, applicants designed and synthesized an additional 8 daidzein analogs that vary in the 7-O substitution (analogs 2 and 3a through 3h). Molecular modeling of representative daidzein analogs and the crystal structure of ERα revealed that daidzein and 3a fit well in the ligand binding pocket of ERα in its estrogen bound configuration. The antiestrogenic 2 was found to dock better in ERα in its antiestrogen-bound configuration. These results demonstrated the structural requirements for the transformation of daidzein from an ER agonist to an antagonist. The most effective analog, 2, may serve as a novel antiestrogen based on the structural motif of a natural isoflavone.

Applicants evaluated the effect of daidzein and daidzein analogs on ERE transcriptional activity, ERα binding affinity, MCF-7 breast cancer cells colonial survival, PgR gene expression and ERα docking. The structure activity relationship studies on these daidzein analogs reveal the progressive loss of an ER agonist activity concurrent to the acquisition of ER antagonistic activity with the substitution of the 7'-OH hydrogen with varying hydrophobic groups. When MCF-7 breast cancer cells were treated with the synthetic analogs, those resulting from hydrogen substitution by isopropyl (3d), isobutyl (3f), cyclopentyl (3g), and pyran- (2), (e.g., branched alkyl or cycloalkyl substitutions) were found to inhibit cell proliferation, estrogen-induced transcriptional activity, and ER regulated progesterone receptor gene expression. In other words, they exhibited significant antiestrogenic properties. However, methyl (3a) and ethyl (3b) substitutions of the hydroxyl proton only led to moderate reduction of the estrogenic activities.

To synthesize 3-(4-Hydroxyphenyl)-8,8-dimethyl-8H-pyrano[2,3-f]chromen-4-one, (2) Glyceollin I was added to a solution of daidzein (1.9 g, 7.2 mmol) in 360 mL of xylene was added 1,1-diethoxy-3-methyl-2-butene (2.4 g, 14.7 mmol) in 15 mL of xylene and 3-picoline (3.7 mmol in 43 mL xylene). The reaction mixture was refluxed at 130° C. for 18 hours. The solvent was evaporated under vacuum and the residue was chromatographed over silica gel using hexanes as eluent. Final product was recrystallized from acetone to give 0.34 g of 3-(4-Hydroxyphenyl)-8,8-dimethyl-8H-pyrano[2,3-f]chromen-4-one as colorless needle crystalline, with an overall yield of 15%.

To synthesize 3-(4-Hydroxyphenyl)-7-methoxychromen-4-one (3a), 7-ethoxyl-4'-hydroxyisoflavone was added to a solution of daidzein (1.27 g, 5 mmol) in 10 mL of DMSO was added anhydrous $K_2CO_3$ (0.9 g, 6.5 mmol) and iodomethane (0.71 g, 5.0 mmol). The reaction mixture was stirred at room temperature for 2 h and then poured into ice water. The resulting mixture was extracted with ethyl acetate. The organic phases were combined, washed with brine, dried over sodium sulfate, filtered, and concentrated under vacuum. The residue was chromatographed over silica gel using hexanes/ethyl acetate (4:1) as eluent. The product was recrystallized from acetone to provide 0.36 g of 3a as a white powder in 27% isolated yield.

To synthesize 3-(4-Hydroxyphenyl)-7-ethoxychromen-4-one (3b), following the procedure used to prepare 3a, reaction of daidzein with bromoethane provided 0.44 g of 3b as a pale yellow solid in 31% yield.

To synthesize 3-(4-Hydroxyphenyl)-7-propoxychromen-4-one (3c), according to the procedure used to prepare 3a, reaction of daidzein with 1-bromopropane provided 0.57 g of 3c in 38% yield as a white powder.

To synthesize 3-(4-Hydroxyphenyl)-7-isopropoxy-chromen-4-one (3d), according to the procedure used to prepare 3a, reaction of daidzein with 2-bromopropane provided 0.26 g of 3d in 18% yield as a white powder.

To synthesize 7-Butoxy-3-(4-hydroxyphenyl)chromen-4-one (3e), by the procedure used to prepare 3a, reaction of daidzein with 1-bromobutane provided 0.66 g of 3e as a white powder in 43% yield.

To synthesize 3-(4-Hydroxyphenyl)-7-isobutoxy-chromen-4-one (3f), by the same procedure used to prepare 3a, reaction of daidzein with 2-bromobutane provided 0.39 g of 3f in 25% yield as a white powder.

To synthesize 7-Cyclopentyloxy-3-(4-hydroxyphenyl)chromen-4-one (3g), according to the procedure used to prepare 3a, reaction of daidzein with bromocyclopentane provided 0.35 g of 3g as a colorless needle crystalline in 22% yield.

To synthesize 7-Hexyloxy-3-(4-hydroxyphenyl)chromen-4-one (3h), according to the procedure used to prepare 3a, reaction of daidzein with 1-bromohexane provided 0.68g of 3h as a colorless crystalline in 40% yield.

To test how structural modifications on the 7-hydroxyl group of daidzein affect estrogenic properties, the ER transcriptional activity induced by the daidzein analogs were measured and compared to daidzein using the estrogen responsive element (ERE) based luciferase reporter gene assay. Results are shown in FIG. 1 where the estrogenic activities of synthetic daidzein analogs were plotted as dose response curves when MCF-7 cells were treated with increasing concentrations of the test compounds. At 1 μM concentration where daidzein induced maximal estrogenic effect in MCF-7 cells, the relative estrogenic potencies of the analogs are seen to decrease in roughly the following order: daidzein>3a>3f>3e>3b≅=3c>3d>2>3g>3h. While this order varied slightly as analog concentrations were increased further to 25 μM, several trends have emerged in the dose-dependent data. First, the parent compound daidzein showed more potent estrogenic activity than any of its derivatives when hydrogen was replaced with alkyl groups with varying chain lengths and configurations. Second, shorter alkyl groups appear to have less effect on the reduction of ER agonist activity than their longer, bulkier counterparts. For example, at 25 μM concentration, 3b (ethyl-), 3a (methyl-), and 3c (n-propyl-) daidzein analogs induced ERE transcriptional activity at 80.4, 70.9, and 38.4%, respectively, retaining greater estrogenic activities than other analogs with longer chain or bulkier substituting groups. Finally, the analog showing little or no estrogen activity, 2, resembles the naturally occurring glyceollin $1^{15}$ in the chromanone moiety, suggesting that the unique ring substitution on the 7O- and 8-chromanone ring is responsible for the diminished estrogenic activity of the modified daidzein.

Figure 2:
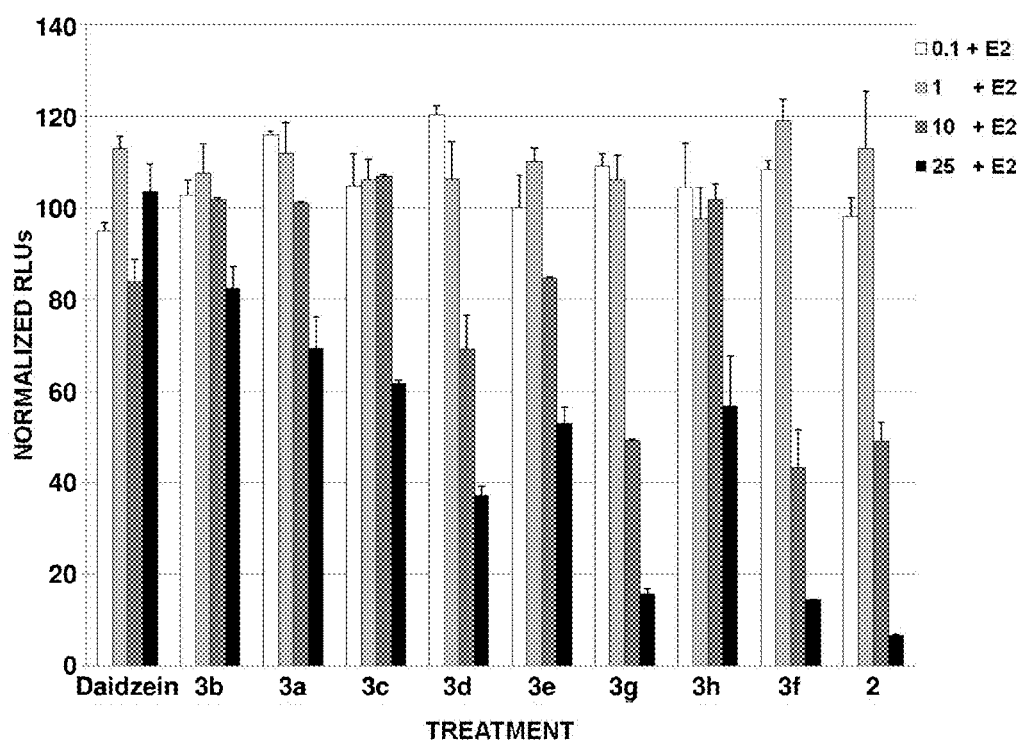
FIG. 2 shows the effects of daidzein and daidzein analogs on $E_2$ stimulation on ERE transcriptional activity in MCF-7 cells. MCF-7 cells were transiently transfected with pGL2-ERE2x-TK-luciferase plasmid. After a 6 h transfection, cells were treated with compounds (DMSO, $E_2$, daidzein and daidzein analogs plus $E_2$) and incubated overnight. Data are represented as relative light units (RLUs) normalized to $E_2$ (100±SEM). The values are the means and the SEM of triplicates from a single experiment and representative for at least three independent experiments. a: significant difference from $E_2$; b: significant difference from $E_2$, $p<0.05$; and c: significant difference from $E_2$ $p<0.001$.

To evaluate the antiestrogenic activities of daidzein analogs, MCF-7 cells were treated with the synthesized compounds at increasing concentrations in the presence of 0.1 nM $E_2$. The luciferase activities of the treated cells were then measured by the ERE reporter gene assay. FIG. 2 shows the dose response curves of MCF-7 cells treated with $E_2$ plus daidzein and its synthetic analogs where the luciferase activity is normalized to 100 for cells treated with 0.1 nM $E_2$ alone. The inhibitory effect of some analogs on $E_2$ became more pronounced as their concentration was increased to 10 μM. At 25 μM, the relative antiestrogenic potencies of the analogs were observed to increase in the following order: daidzein<3b<3a<3c<3h<3e<3d<3g<3f<2. The analogs that reduced estradiol-dependent luciferase activity by greater than 60% at 25 μM included 2, 3f, 3g, and 3d, of which 2 was the most effective antiestrogen, completely blocking ERE activity at 25 μM. In contrast, analogs 3a, 3b, 3c, 3h, and 3e decreased $E_2$ induced transcriptional activity by less than 47% at the highest ligand concentration. Compared with estrogenic activity assay results, the analogs showing strong antiestrogenic activity exhibited little or no estrogen activity. For example, 2, 3f, and 3g all induced negligible ERE activity, but they behaved as potent estrogen inhibitors (FIG. 1 and FIG. 2). On the other hand, the strongest estrogenic analogs, 3a, 3b, and 3c (FIG. 2), failed to inhibit 50% ERE activity in the presence of $E_2$ at all concentrations tested. Taken together, the alkyl substituted daidzein analogs can be viewed in two groups in terms of their ER mediated transcriptional activities. The first group (3a, 3b, and 3c) where the 7-OH of daidzein is alkoxylated by the methyl, ethyl, and n-propyl group, respectively, has retained much of the estrogenic function of daidzein. The second group, consisting of 2, 3g, 3f, and to a lesser extent 3d, has been transformed into potent antiestrogens. This complete reversal from estrogenic to antiestrogenic activity in certain daidzein analogs highlights the importance of the structure of 7O-substitution in determining the ligand's interaction with the estrogen receptor. It is also interesting to note the significant difference in ERE activity between the i-propyl (3d) and n-propyl (3c) substituted analog, suggesting that a branched alkyl group may provide a better binding mechanism toward the ER.

Figure 3:
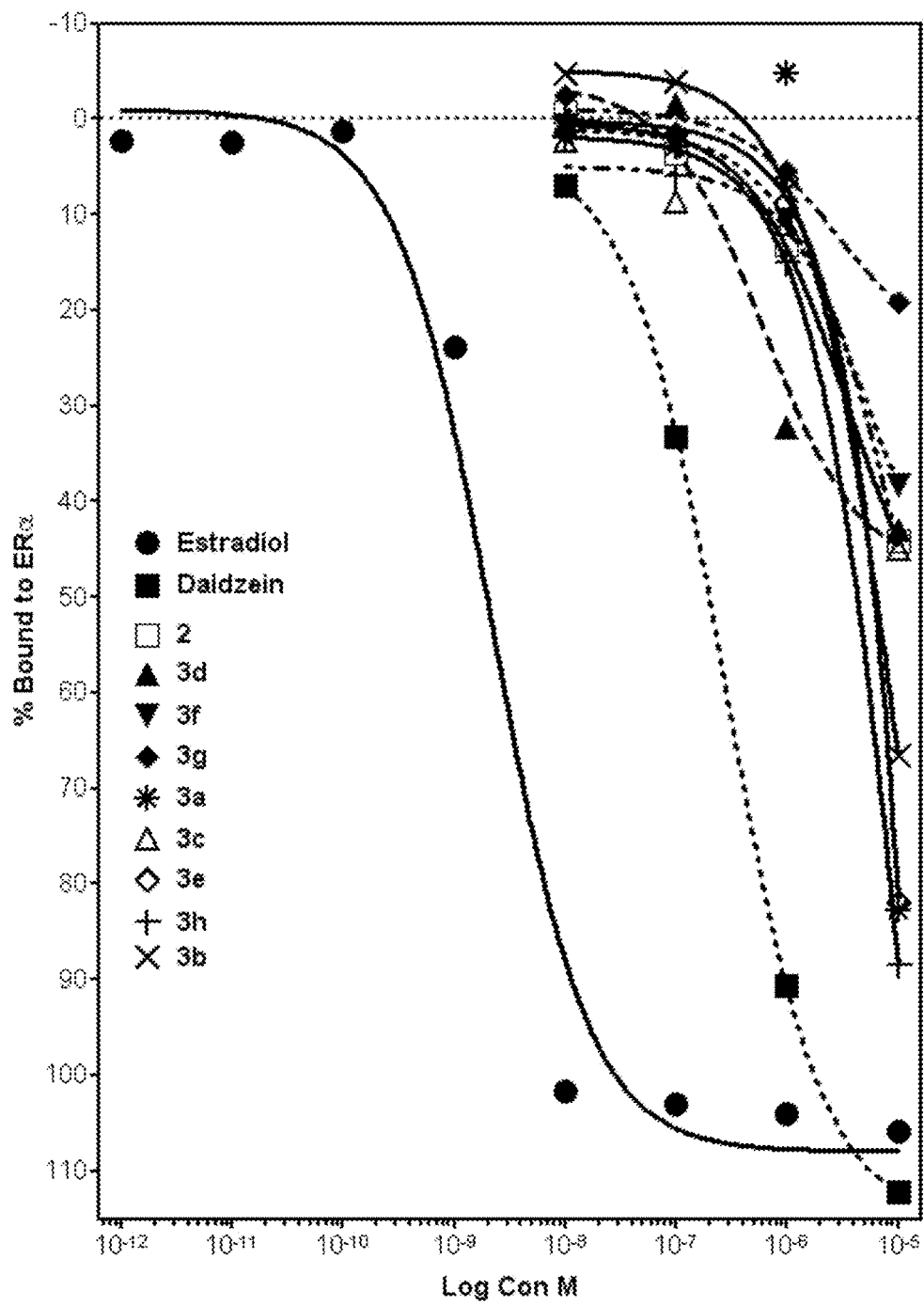
FIG. 3 shows relative binding affinity of daidzein and daidzein analogs for ERα. Increasing concentrations of daidzein analogs were added to the ER complex and compared to $E_2$. Data points and error bars represent the mean±SEM of at least three experiments (n=3) for each concentration tested. ($p<0.05$).

In an attempt to understand the biological activity of the synthesized daidzein analogs, the ability of each daidzein analogs to bind to ERα was examined using a competitive binding assay with fluorescent detection (FIG. 3). Analysis of the competition binding curve yielded $IC_{50}$ values, representing the concentration of unlabeled ligand required to displace 50% of the tracer from the ERα). Unlabeled $E_2$ was used as a reference and its displacement of 50% tracer $E_2$ bound to ERα occurred at 1.5 nM. Compared to daidzein, which has an IC50 value of 0.45 μM, none of the analogs displayed higher binding affinities towards the estrogen receptor. The maximal % bound to ERα for the analogs are summarized in Table 1. At 10 μM ligand concentration, four analogs showed over 50% bound ERα, i.e., 3a, 3b, 3e, and 3h while the rest of analogs appeared to have lower binding affinities towards the ER. The binding data are partially consistent with the observation that structural modifications on the 7O-position of daidzein reduced more estrogenic potency of the analogs to various degrees at lower concentrations (10 μM) than at higher doses (25 μM). However, the reason for higher binding affinities exhibited by 3h and 3e which are neither estrogenic nor antiestrogenic is unclear. The binding curves suggest that at higher concentrations (e.g., 25 μM as used in the luciferase reporter assay), the degree of binding to ER by several analogs may rapidly approach that of daidzein. This is also consistent with the fact that both estrogenic (3a, 3b, and 3c) and antiestrogenic (2, 3f, 3g) activities of the analogs reached maximal levels at 25 μM (FIGS. 1 and 2). For example, 3a reached 38% ERE activity at 10 μM, comparing to a 83% binding to ER; at 25 μM, its ERE activity increased dramatically to 70.9% (FIG. 1). The binding curve for 3a confirmed this rapid increase in estrogenic activity as its % bound value appear to approach that of daidzein. Notably, for antiestrogenic compounds, binding affinities to ERα did not appear to correlate well with their ability to inhibit $E_2$ induced ERE activity.

Figure 4A:
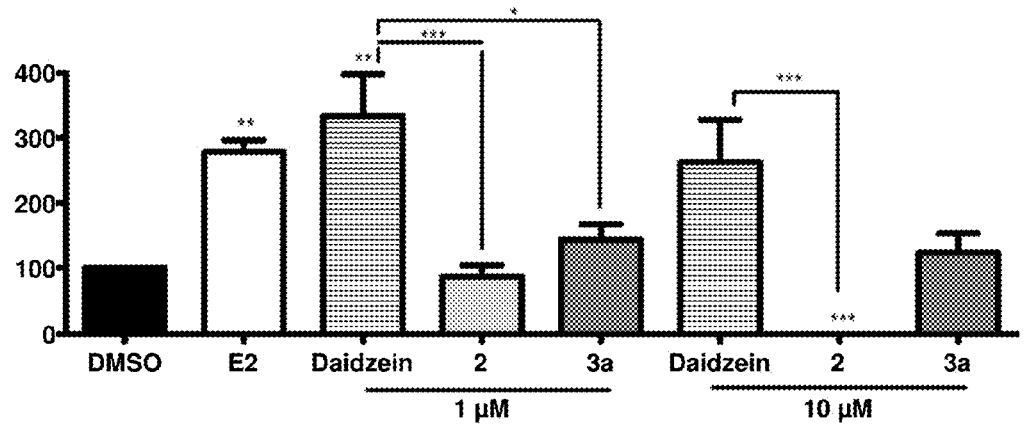
FIG. 4A and FIG. 4B show effects of daidzein, 2 and 3 a on $E_2$ stimulation on colony formation on MCF-7 Cells. MCF-7 cells were placed in phenol red-free DMEM supplemented with 5% dextran-coated charcoal-treated FBS for 48 h before plating. MCF-7 cells (1000) were plated in six well plates. Forty eight hours later, cells were treated with DMSO (vehicle), $E_2$, daidzein and daidzein analogs (at 1 μm and 10 μM) (see FIG. 4A) and $E_2$, $E_2$+ daidzein and $E_2$+ daidzein analogs (at 1 μm and 10 μM) (see FIG. 4B). Colonies of >50 cells were counted as positive. Results are normalized to percentage of clonogenic survival from DMSO control cells. The values are the means and the SEM of triplicates from a single experiment and representative for at least three independent experiments. Significant difference from vehicle control (FIG. 4A) and $E_2$ (FIG. 4B), *$p<0.05$, $p<0.01$ and *$p<0.001$; Tukey test.
Figure 4B:
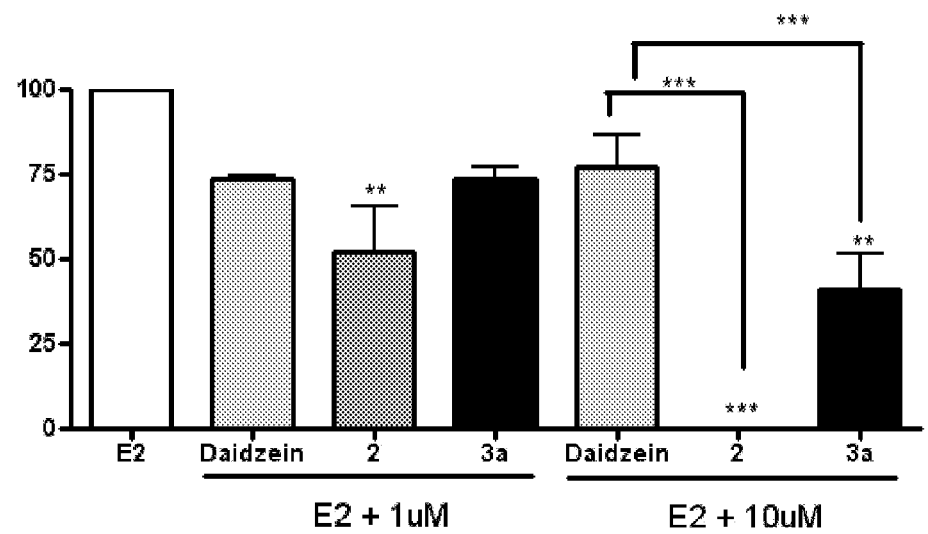

To further evaluate the estrogenic or antiestrogenic activities of the daidzein analogs determined from the ERE transcriptional assay, two analogs, 3a and 2, were selected for further test by a clonogenic assay for their ability to inhibit the estradiol-induced proliferation of MCF-7 cells. As discussed earlier, 3a behaved as an estrogen with a slightly lower potency than daidzein, whereas 2 acted as an antiestrogen that was able to inhibit 100% ER mediated transcriptional activity. In the colony assay MCF-7 cells were treated with increasing concentrations of daidzein, 2, and 3a in the presence or absence of 0.1 nM $E_2$. Results are illustrated in FIG. 4 where estrogen-dependent cell growth was normalized to 100 for the control (DMSO) (FIG. 4A) or for $E_2$ alone (FIG. 4B). The addition of 0.1 nM $E_2$ to the culture media resulted in an approximately 3-fold increase in the clonogenicity of the MCF-7 cells compared to DMSO treated controls. At 1 μM, daidzein also promoted the clonogenicity of MCF-7 cells by over 3-fold, while 3a increased cell proliferation by 43%, confirming that 3a is a weaker estrogen than daidzein, a direct consequence of the replacement of 7-hydroxy group by 7-methoxy group. In contrast, 2 inhibited the clonogenicity by 15% at the same concentration, demonstrating its antiestrogenic property at 1 μM concentration. When concentration was raised to 10 μM, daidzein and 3a continued to increase the clonogenicity of MCF-7 cells by 2.5 times and 24%, respectively. Analog 2, however, completely blocked cell clonogenicity at 10 μM. FIG. 4B illustrates the effect of daidzein and the two analogs on cell clonogenicity in the presence of 0.1 nM $E_2$. Even in the presence of 0.1 nM estradiol, 2 at 10 μM was able to inhibit the clonogenicity of MCF-7 cells completely. Thus, the colony assay results clearly demonstrated the divergence of hormonal activities in daidzein analogs by simple modifications of the 7-OH group of daidzein.

Figure 5:
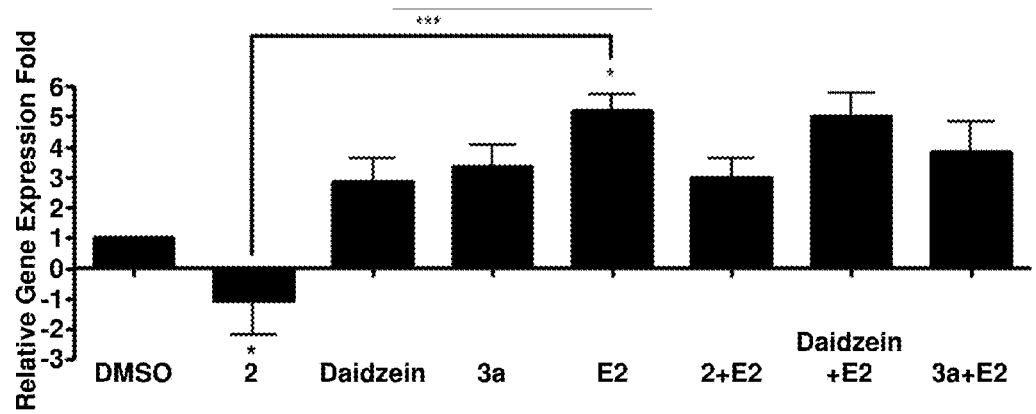
FIG. 5 show effects of daidzein, 2 and 3 a on PgR expression. Total RNA was isolated from MCF-7 cells, reverse-transcribed into cDNA and subjected to real-time RT-PCR analysis for quantification. Treatment on MCF-7 cells was as follows: DMSO (vehicle), daidzein, 2, 3a, $E_2$, daidzein+$E_2$, 2+$E_2$, 3a+$E_2$ (10 μm and 10 μM+$E_2$). Results are expressed as the mean unit±SEM. (*$p<0.05$; $p<0.01$; *$p<0.001$) with significant differences from vehicle control.

To further examine the differing hormonal activities of daidzein analogs, ER-mediated gene expression of progesterone receptor (PgR) was monitored by quantitative real time RT-PCR in MCF-7 cells treated with daidzein, 2 (an antiestrogenic analog), and 3a (an estrogenic analog) (FIG. 5). Progesterone receptor (PgR) is an estrogen-responsive gene, whose expression has been shown to indicate a responsive estrogen receptor pathway. The expression of PgR mRNA in MCF-7 cells that were treated with DMSO (control) and daidzein, 2 and 3a either in the presence or absence of $E_2$ were determined. When treated with ligands only, daidzein and 3a induced 3-fold increase in PgR expression compared with control, while a 5-fold increase was induced by $E_2$. However, 2 caused a decrease in PgR expression compared with DMSO, demonstrating its non-estrogenic nature. When MCF-7 cells were treated with the ligands in the presence of 0.1 nM $E_2$, both daidzein and 3a were able to promote the level of PgR expression by 5- and 4-fold, respectively. In contrast, 2 inhibited the $E_2$ induced PgR expression by reducing its upregulation from 5-fold to 3-fold.

Figure 6A:
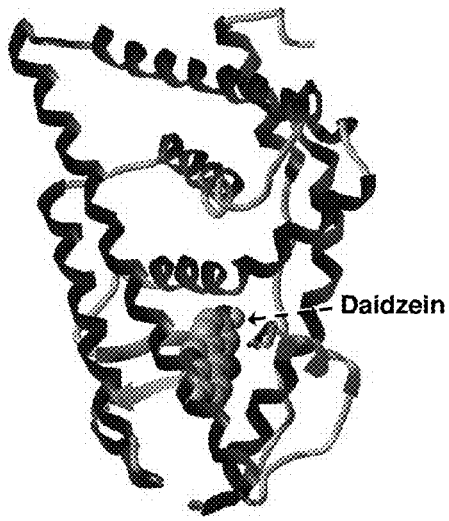
FIG. 6A, FIG. 6B, FIG. 6C, FIG. 6D, FIG. 6E, and FIG. 6F show molecular modeling of daidzein analogs 2 and 3a. Binding modes of daidzein (see FIG. 6A), 2 (see FIG. 6B) to estrogenic conformer of ERα and 2 (see FIG. 6C) to antiestrogenic conformer of ERα, wherein the protein is depicted as ribbon/tube model colored by secondary structure and the compounds are shown as spacefill models.
Figure 6B:
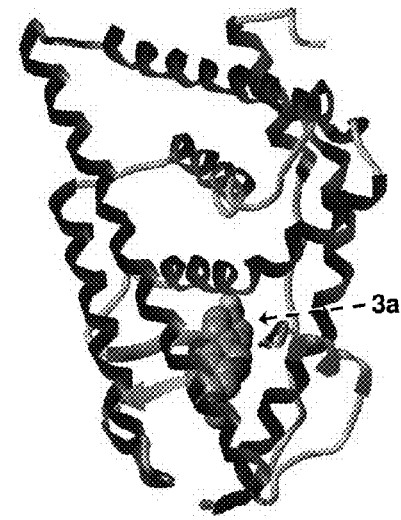
Figure 6C:
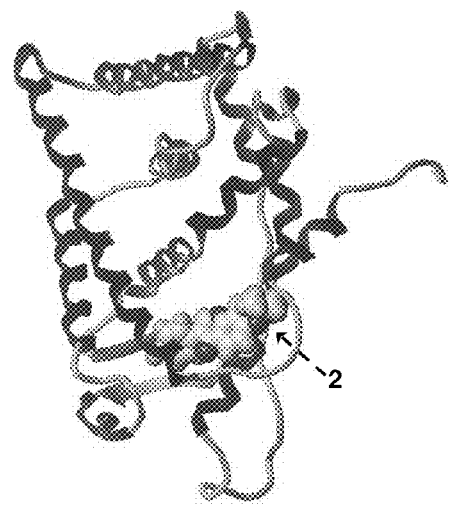
Figure 6D:
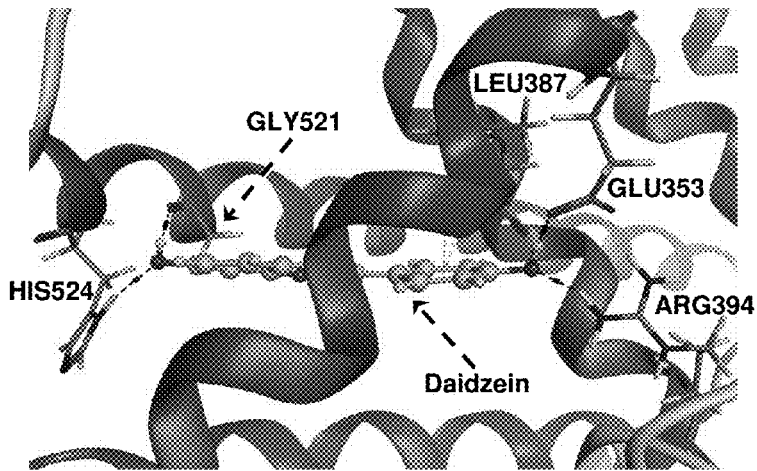
Figure 6E:
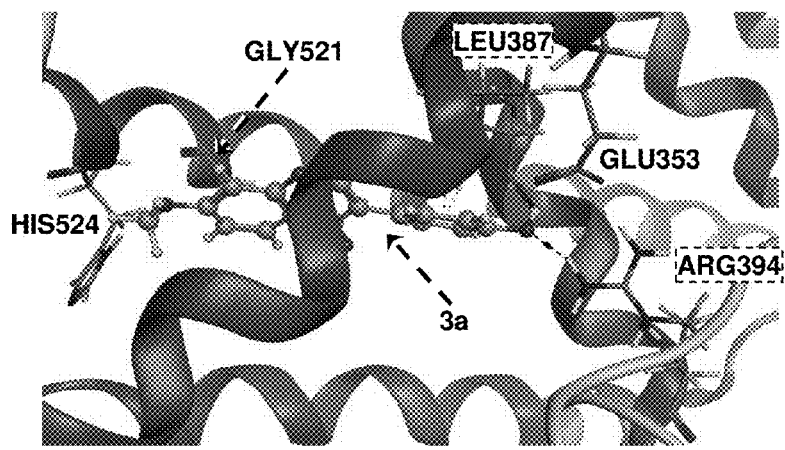
Figure 6F:
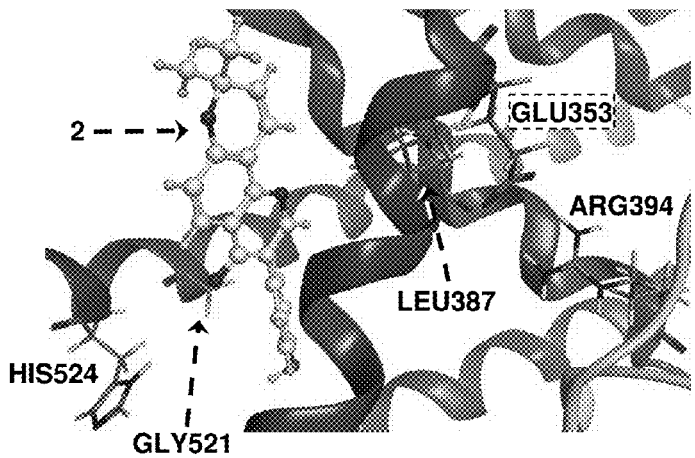
Figure 7:
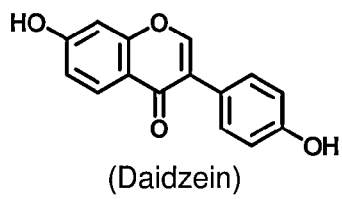
FIG. 7 shows the structure of daidzein.
Figure 8:
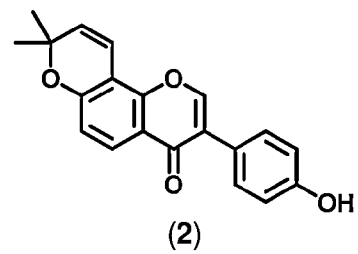
FIG. 8 shows the structure of the novel daidzein analog, 3-(4-Hydroxyphenyl)-8,8-dimethyl-8H-pyrano[2,3-f]chromen-4-one (2).
Figure 9:
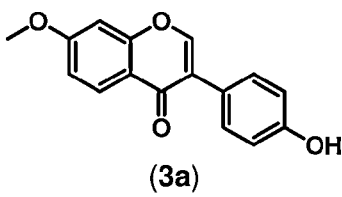
FIG. 9 shows the structure of the novel daidzein analog, 3-(4-Hydroxyphenyl)-7-methoxychromen-4-one (3a).
Figure 10:
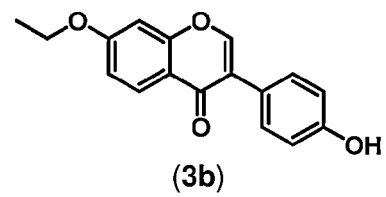
FIG. 10 shows the structure of the novel daidzein analog, 3-(4-Hydroxyphenyl)-7-ethoxychromen-4-one (3b).
Figure 11:
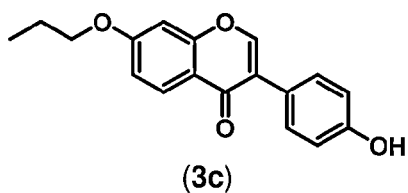
FIG. 11 shows the structure of the novel daidzein analog, 3-(4-Hydroxyphenyl)-7-propoxychromen-4-one (3c).
Figure 12:
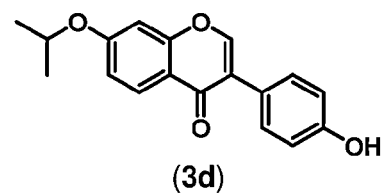
FIG. 12 shows the structure of the novel daidzein analog, 3-(4-Hydroxyphenyl)-7-isopropoxychromen-4-one (3d).
Figure 13:
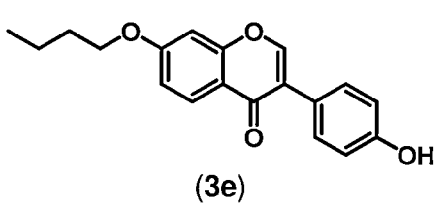
FIG. 13 shows the structure of the novel daidzein analog, 7-Butoxy-3-(4-hydroxyphenyl)chromen-4-one (3e).
Figure 14:
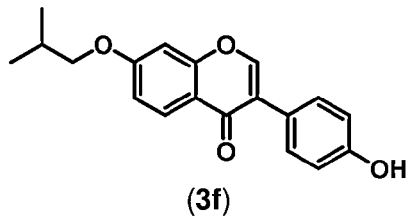
FIG. 14 shows the structure of the novel daidzein analog, 3-(4-Hydroxyphenyl)-7-isobutoxychromen-4-one (3f).
Figure 15:
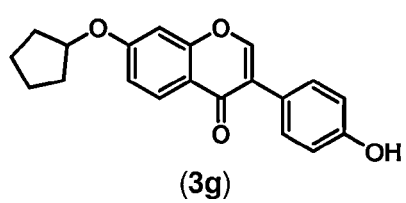
FIG. 15 shows the structure of the novel daidzein analog, 7-Cyclopentyloxy-3-(4-hydroxyphenyl)chromen-4-one (3g).
Figure 16:
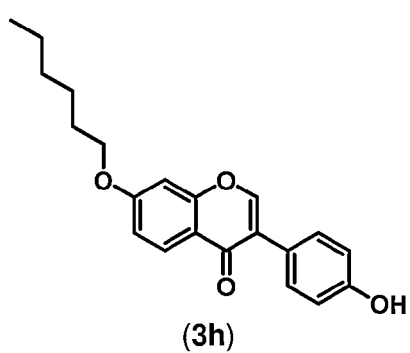
FIG. 16 shows the structure of the novel daidzein analog, 7-Hexyloxy-3-(4-hydroxyphenyl)chromen-4-one (3h).
Figure 17:
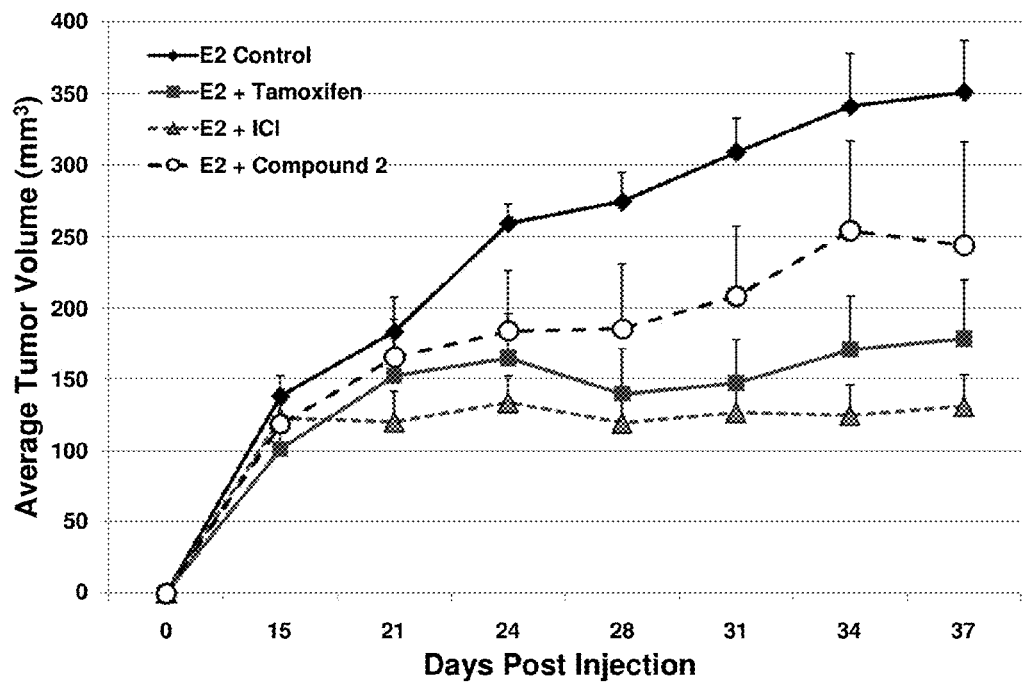
FIG. 17 shows anti-estrogenic effects of analog 2 on MCF-7 cell tumorigenesis in vivo. 4-6 week old ovariectomized female Nu/Nu mice were injected bilaterally in the mammary fat pad (MFP) with $5 \times 10^6$ MCF-7 cells in matrigel (reduced factor). All animals were implanted with a 17β-estradiol pellet (0.72 mg, 60-day release) subcutaneously in the lateral area of the neck at the time of cell injection. Tumors were allowed to form and at day 15 post cell injection mice were randomized into groups (n=5). Animals were treated daily with i.p. injections of either vehicle (1:5 DMSO/PBS) or analog 2 (50 mg/kg/animal). Tamoxifen animals were implanted with a slow release tamoxifen pellet in the lateral area of the neck (opposite side from E2 pellet). ICI animals were given a onetime i.p. injection of ICI 182,780 (5 mg in castor oil). Tumor size was measured 3 times weekly using digital calipers. Data represented as mean tumor volume±SEM.

The estrogenic analog 3a and antiestrogenic analog 2, along with the parent compound daidzein were subjected to docking studies (see FIGS. 6A-F). To understand the nature of their interactions with ERα, two protein conformations were selected as template coordinates for the docking studies. It has been well established that the binding mode of ligand to the estrogen receptor causes structural perturbations in and around the ligand binding pocket resulting in two protein conformations that contribute to the estrogenic or antiestrogenic effects.[18, 19, 20] Two such representative structures—3ERD (ERα bound to the agonist diethylstilbestrol) and 3ERT (ERα bound to the antagonist 4-hydroxytamoxifen) were taken as protein templates. The compounds were docked to the template protein structures using the Surflex docking program. The Surflex scoring and the binding postures for the compounds daidzein and 3a were comparable for the estrogenic and antiestrogenic protein conformations with a slight preference to the estrogenic conformation. The binding modes of daidzein and 3a for the estrogenic protein conformation are represented in FIGS. 6A and 6B. Daidzein forms hydrogen bonds with GLU353, ARG394, GLY521 and HIS524 (FIG. 6D). 3a forms hydrogen bonds with LEU387, ARG394 and HIS524 (FIG. 6E), resulting in fewer hydrogen bonding interactions than daidzein which could account for its weaker estrogenic activity. Analog 2 docked to the antiestrogenic conformation of the protein with a significantly better Surflex score than when docked to the estrogenic conformation of the protein which implies that it can have antiestrogenic property. The binding posture of 2 (FIGS. 6C and 6F) for the antiestrogenic protein conformation was similar to that of other ERα antagonists tamoxifen and raloxifene. These docking studies further confirm the nature of estrogenic and antiestrogenic activity exhibited by the compounds 3a and 2.

Due to the anti-estrogenic effects of analog 2 on MCF-7 cells observed in the in vitro biological assays, this analog was selected for further testing of estrogen stimulated MCF-7 cell tumorigenesis using a xenograft model. Ovariectomized female immunocompromised mice were injected with MCF-7 cells and supplemented with exogenous estrogen pellets. Once tumors were palpable animals were treated with analog 2, tamoxifen, or ICI and tumor volume compared to vehicle control animals. At day 37 post cell injection a decrease in tumor volume was observed in all treatment groups compared to control (351.17±43.88). Analog 2 treatment resulted in reduced tumor volumes similar to tamoxifen treated animals (241.53±68.29 and 178.12±41.18 mm3 respectively), while treatment with the pure anti-estrogen ICI 182,780 was most effective in attenuating estrogen-induced tumorigenesis (130.95±23.49). These results confirm that the anti-estrogenic properties of analog 2 observed in vitro extend to in vivo conditions as well.

Xenograft experiments were conducted using previously published protocols. Briefly, 4-6 week old female ovariectomized NU/Nu mice were obtained from Charles River Laboratories (Wilmington, Mass.). The animals were allowed a period of adaptation in a sterile and pathogen-free environment with phytoestrogen-free food and water ad libitum. MCF-7 cells were harvested in the exponential growth phase using a PBS/EDTA solution and washed. Mice were injected bilaterally in the mammary fat pad (M.F.P) with $5 \times 10^6$ viable cells suspended in 50 μL sterile PBS mixed with 100 μL Matrigel (reduced factor; BD Biosciences, Bedford, Mass.). 17β-estradiol pellets (0.72 mg, 60-day release; Innovative Research of America, Sarasota, Fla.) were implanted subcutaneously in the lateral area of the neck using a precision trochar (10 gauge) at the time of cell injection. All procedures in animals were carried out under anesthesia using a mix of isofluorane and oxygen delivered by mask. Tumors were allowed to form and at day 15 post cell injection mice were randomized into groups of 5 mice each. Mice were treated daily with intra-peritoneal injections of either vehicle (1:5 DMSO/PBS) or analog 2 (50 mg/kg/animal) for 21 days. Tamoxifen animals were implanted with a slow release tamoxifen pellet in the lateral area of the neck on the opposite side from the estrogen pellet. ICI animals were given a onetime intra-peritoneal injection of ICI 182,780 (5 mg in castor oil) on day 15 post cell injection. Tumor size was measured 3 times weekly using digital calipers. The volume of the tumor was calculated using the following formula: 4/3 $\pi LS^2$ (L=larger radius; S=shorter radius). All procedures involving animals were conducted in compliance with State and Federal laws, standards of the U.S. Department of Health and Human Services, and guidelines established by Tulane University Animal Care and Use Committee. The facilities and laboratory animals program of Tulane University are accredited by the Association for the Assessment and Accreditation of Laboratory Animal Care.

Data were summarized as the Mean±Standard Error of the Mean (SEM) using the Graph Pad Prism V.4 software program. Analysis of variance models were employed to compare relative ERE transcriptional reporter assays between controls versus treatment. A Tukey post-test was performed to compare differences between groups where a p value<0.05 was considered significant.

Figure 18:
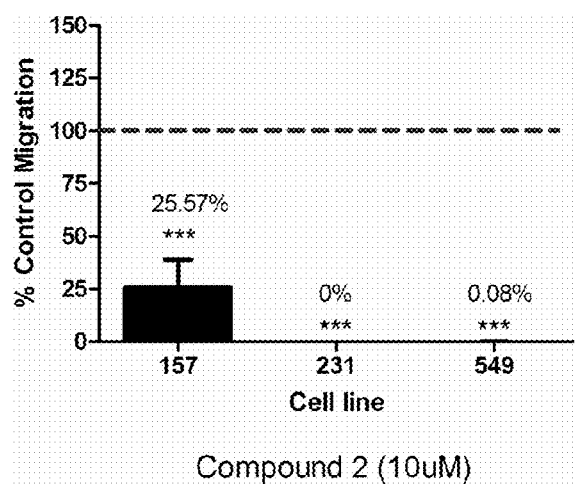
FIG. 18 shows the results of an in vitro migration assay of triple-negative breast carcinoma (TNBC) cell lines treated with analog 2.

As shown in FIG. 18, migration assays were performed per manufacturer's instructions (BD Falcon) and as previously published (Rhodes et al, 2010). TNBC cells were seeded ($2.5 \times 10^4$ in 500 μl 10% DMEM) in the upper chamber of a 24 well transwell system. DMEM supplemented with FBS (10%) was used as a chemoattractant in the lower wells. After 24 hours of treatment (DMSO or analog 2 10 μM), membranes were scrubbed, stained with 0.1% crystal violet, and the number of migrated cells analyzed by microscopy. Data represented as normalized means of triplicate experiments±SEM. All three TNBC cell lines tested (MDA-MB-157, MDA-MB-231, and BT-549) revealed a significant decrease (25.57%, 0%, and 0.08% respectively, p<0.001) in the number of migrated cells compared to control (normalized to 100%). The TNBC phenotype is characterized by highly aggressive and migratory cells. The ability of analog 2 to inhibit this migration indicates its potential as a novel anti-metastatic therapeutic in the triple-negative breast carcinoma setting.

Figure 19:
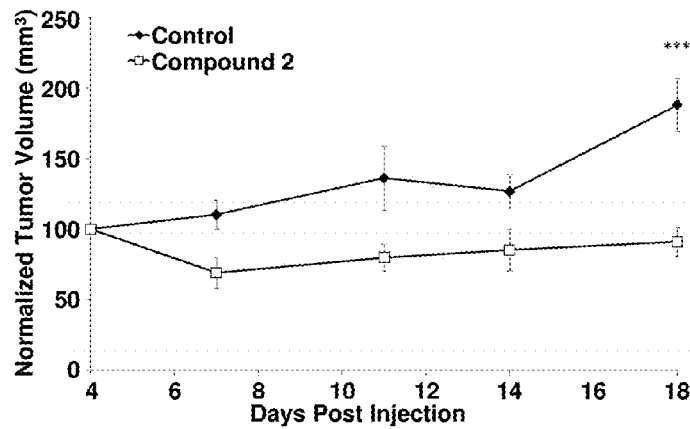
FIG. 19 shows the effects of analog 2 treatment on tumor volume in mice.
Figure 20A:
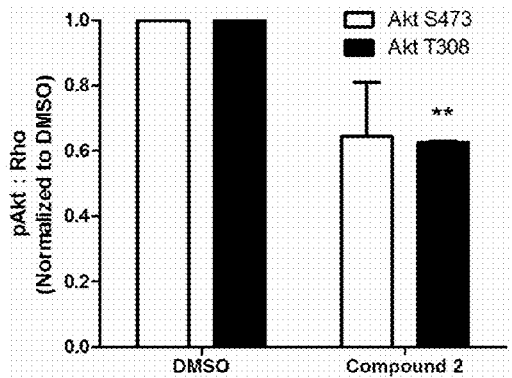
FIG. 20 (A-C) shows that the effects of analog 2 on TNBC may be mediated via alterations in the PI3K/AKT/mTOR pathway.
Figure 20B:
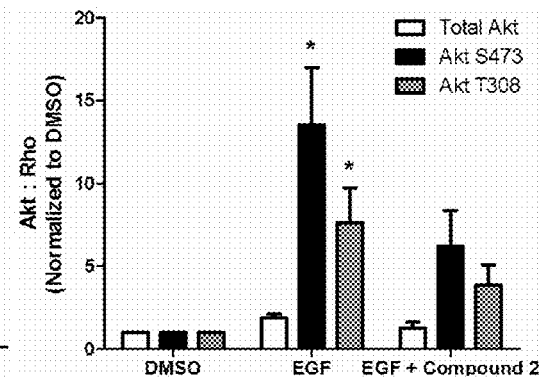
Figure 20C:
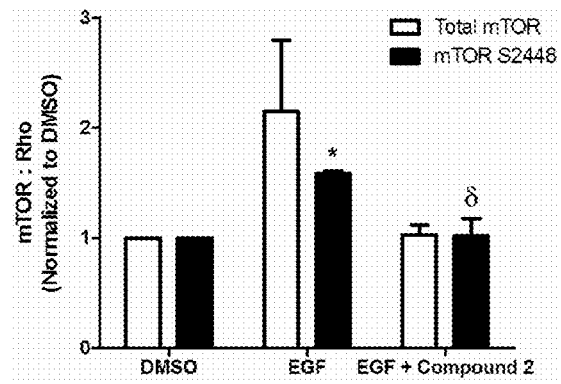

FIG. 19 shows that analog 2 dramatically reduces tumor volume in female mice. 4-6 week old female CB-17/SCID mice were allowed a period of adaptation in a sterile and pathogen-free environment with phytoestrogen-free food and water ad libitum. MDA-MB-231 cells were harvested in the exponential growth phase using a PBS/EDTA solution and washed. Mice were injected bilaterally in the mammary fat pad (MFP) with $5 \times 10^6$ viable cells suspended in 50 μL sterile PBS mixed with 100 μL Matrigel (reduced factor; BD Biosciences, Bedford, Mass.). Tumors were allowed to form, and at day 4 post cell injection mice were randomized into groups of 5 mice each. Mice were treated daily with intra-peritoneal (IP) injections of either vehicle (DMSO) or analog 2 (50 mg/kg/animal/day) for 14 days. External tumor size was measured using digital calipers and tumor volume calculated using the formula: $4/3 \pi LS^2$ (L=larger radius; S=shorter radius). At necropsy, animals were euthanized by cervical dislocation after exposure to $CO_2$. Seven days after cell injection, and after three days' treatment with analog 2, the tumor volumes of treated mice were statistically less than those of control mice. This trend continued until the mice were euthanized at day 18, where tumor volume for control mice averaged $188 \pm 18.78$ mm$^3$ and the tumor volume for mice treated with analog 2 averaged $91.11 \pm 10.15$ mm$^3$. These results confirm that the anti-cancer effects of analog 2 on TNBC observed in vitro extend to in vivo conditions as well. The results also indicate that pharmaceutical compositions comprising at least one novel daidzein analog are useful in treatment of cancer, and that their utility is expected to be associated with amelioration of symptoms, improvement in general well being and quality of life, and improvement in other associated conditions like anemia, neutropenia, pain, and dysphagia.

The at least one novel daidzein analog may be administered in an amount from about 0.1 to about 500, about 1 to about 500, about 10 to about 500, about 100 to about 500, about 250 to about 500, about 0.1 to about 100, about 1 to about 100, about 10 to about 100, about 25 to about 50 to about 100, about 0.1 to about 50, about 1 to about 50, about 5 to about 50, about 10 to about 50, about 20 to about 50, about 30 to about 50, about 40 to about 50, and preferably about 50 mg/kg/mammal/day. The at least one novel daidzein analog may be provided as a solid or liquid product for oral delivery; said product may comprise a concentrate, a dried powder, a liquid, a solution, a suspension, an emulsion, a syrup, time release technology, a capsule, a tablet, a pellet, or a pill. The at least one novel daidzein analog may be provided as a product for parenteral administration, including intravenous, intradermal, intramuscular, intraperitoneal, and subcutaneous administration.

The effects of analog 2 on TNBC may be mediated via alterations in the PI3K/AKT/mTOR pathway. After 72 hours in 5% charcoal-stripped fetal bovine serum (CSFBS) DMEM phenol-free medium, MDA-MB-231 cells were re-fed with either medium-containing vehicle, analog 2 (10 μM, 4 hours), analog 2 (4 hours) followed by EGF stimulation (50 ng/mL, 30 minutes), or EGF alone (30 minutes). Membranes were probed with primary antibodies according to manufacturers' protocol. Antibodies: phosho-AKT (S473 and T308), mTOR (52448), and corresponding total protein antibodies (Cell Signaling), using rho as a loading control (Santa Cruz). Treatment of the triple-negative MDA-MB-231 cells with analog 2 resulted in significant decreases in phospho-levels of AKT at both the S473 and T308 sites. Additionally, analog 2 was able to significantly abrogate the effects of EGF stimulation on AKT and mTOR phosphorylation in the MDA-MB-231 cells. These results indicate that the effects of analog 2 on TNBC may be mediated, at least in part, via alterations in the PI3K/AKT/mTOR pathway.

What is claimed is:

1. A pharmaceutical composition, wherein said composition comprises at least one daidzein analog selected from the group consisting of:
    (a) 3-(4-Hydroxyphenyl)-8,8-dimethyl-8H-pyrano[2,3-f] chromen-4-one;
    (b) 3-(4-Hydroxyphenyl)-7-ethoxychromen-4-one
    (c) 3-(4-Hydroxyphenyl)-7-propoxychromen-4-one;
    (d) 3-(4-Hydroxyphenyl)-7-isopropoxychromen-4-one;
    (e) 7-Butoxy-3-(4-hydroxyphenyl)chromen-4-one;
    (f) 3-(4-Hydroxyphenyl)-7-isobutoxychromen-4-one;
    (g) 7-Cyclopentyloxy-3-(4-hydroxyphenyl)chromen-4-one; and
    (h) 7-Hexyloxy-3-(4-hydroxyphenyl)chromen-4-one;
    wherein said at least one daidzein analog induces less estrogenic activity than daidzein.

2. A method of minimizing or treating estrogen-dependent cancer or tumor growth, wherein said cancer or tumor growth is selected from breast cancer, in an animal in need thereof, comprising administering to said animal a composition comprising an effective amount of at least one daidzein analog selected from the group consisting of:
    (a) 3-(4-Hydroxyphenyl)-8,8-dimethyl-8H-pyrano[2,3-f] chromen-4-one;
    (b) 3-(4-Hydroxyphenyl)-7-ethoxychromen-4-one
    (c) 3-(4-Hydroxyphenyl)-7-propoxychromen-4-one;
    (d) 3-(4-Hydroxyphenyl)-7-isopropoxychromen-4-one;
    (e) 7-Butoxy-3-(4-hydroxyphenyl)chromen-4-one;
    (f) 3-(4-Hydroxyphenyl)-7-isobutoxychromen-4-one;
    (g) 7-Cyclopentyloxy-3-(4-hydroxyphenyl)chromen-4-one; and
    (h) 7-Hexyloxy-3-(4-hydroxyphenyl)chromen-4-one;
    wherein said at least one daidzein analog induces less estrogenic activity than daidzein.

3. The composition of claim 1 wherein the at least one daidzein analog is the compound 3-(4-Hydroxyphenyl)-8,8-dimethyl-8H-pyrano[2,3-f] chromen-4-one.

4. The composition of claim 1 wherein the at least one daidzein analog is the compound 3-(4-Hydroxyphenyl)-7-ethoxychromen-4-one.

5. The composition of claim 1 wherein the at least one daidzein analog is the compound 3-(4-Hydroxyphenyl)-7-propoxychromen-4-one.

6. The composition of claim 1 wherein the at least one daidzein analog is the compound 3-(4-Hydroxyphenyl)-7-isopropoxychromen-4-one.

7. The composition of claim 1 wherein the at least one daidzein analog is the compound 7-Butoxy-3-(4-hydroxyphenyl)chromen-4-one.

8. The composition of claim 1 wherein the at least one daidzein analog is the compound 3-(4-Hydroxyphenyl)-7-isobutoxychromen-4-one.

9. The composition of claim 1 wherein the at least one daidzein analog is the compound 7-Cyclopentyloxy-3-(4-hydroxyphenyl)chromen-4-one.

10. The composition of claim 1 wherein the at least one daidzein analog is the compound 7-Hexyloxy-3-(4-hydroxyphenyl)chromen-4-one.

11. The method of claim 2 wherein the at least one daidzein analog is the compound 3-(4-Hydroxyphenyl)-8,8-dimethyl-8H-pyrano[2,3-f]chromen-4-one.

12. The method of claim 2 wherein the at least one daidzein analog is the compound 3-(4-Hydroxyphenyl)-7-ethoxychromen-4-one.

13. The method of claim 2 wherein the at least one daidzein analog is the compound 3-(4-Hydroxyphenyl)-7-propoxychromen-4-one.

14. The method of claim 2 wherein the at least one daidzein analog is the compound 3-(4-Hydroxyphenyl)-7-isopropoxychromen-4-one.

15. The method of claim 2 wherein the at least one daidzein analog is the compound 7-Butoxy-3-(4-hydroxyphenyl)chromen-4-one.

16. The method of claim 2 wherein the at least one daidzein analog is the compound 3-(4-Hydroxyphenyl)-7-isobutoxychromen-4-one.

17. The method of claim 2 wherein the at least one daidzein analog is the compound 7-Cyclopentyloxy-3-(4-hydroxyphenyl)chromen-4-one.

18. The method of claim 2 wherein the at least one daidzein analog is the compound 7-Hexyloxy-3-(4-hydroxyphenyl)chromen-4-one.

19. The composition of claim 1 wherein said composition comprises a product for oral delivery, said product form being selected from the group consisting of a dried powder, a liquid, a capsule, a pellet, and a pill.

20. The composition of claim 1 wherein said composition comprises a product for parenteral administration selected from the group consisting of intravenous, intradermal, intramuscular, and subcutaneous administration.

21. The composition of claim 1 further comprising at least one carrier, at least one binder, at least one diluent, at least one excipient, or mixtures thereof.

22. The method of claim 2 wherein said composition is in the form of a product for oral delivery, said product form being selected from the group consisting of dried powder, liquid, capsule, pellet, or pill.

23. The method of claim 2 wherein said composition is in the form of a product for parenteral administration selected from the group consisting of products for intravenous, intradermal, intramuscular, and subcutaneous administration.

24. The method of claim 2 wherein said composition further comprises at least one carrier, at least one binder, at least one diluent, at least one excipient, or mixtures thereof.

\* \* \* \* \*